United States Patent [19]

Huberti

[11] Patent Number: 5,042,504
[45] Date of Patent: Aug. 27, 1991

[54] DEVICE FOR MONITORING LOADS EXERTED ON PARTS OF THE BODY

[76] Inventor: Helmut Huberti, Hauptstrasse 33, D-6630 Saarlouis, Fed. Rep. of Germany

[21] Appl. No.: 434,676
[22] PCT Filed: Apr. 27, 1988
[86] PCT No.: PCT/EP88/00354
§ 371 Date: Oct. 25, 1989
§ 102(e) Date: Oct. 25, 1989
[87] PCT Pub. No.: WO88/08275
PCT Pub. Date: Nov. 3, 1988

[30] Foreign Application Priority Data

Apr. 29, 1987 [DE] Fed. Rep. of Germany ....... 3714218

[51] Int. Cl.⁵ .............................. A61B 5/11
[52] U.S. Cl. ................................... 128/779
[58] Field of Search .................... 128/774, 779, 782

[56] References Cited

U.S. PATENT DOCUMENTS

| | | | |
|---|---|---|---|
| 2,290,387 | 7/1942 | Schwartz | 128/779 |
| 4,152,748 | 5/1979 | Arkans | 128/779 |
| 4,195,643 | 4/1980 | Pratt, Jr. | 128/779 |
| 4,250,888 | 2/1981 | Grosskopf | 128/702 |
| 4,353,375 | 10/1982 | Colburn et al. | 128/782 |
| 4,618,822 | 10/1986 | Hansen | 128/782 |
| 4,745,930 | 5/1988 | Confer | 128/779 |
| 4,830,021 | 5/1989 | Thornton | 128/779 |

FOREIGN PATENT DOCUMENTS 2273257 12/1975 France .
2513508 4/1983 France .
8604802 8/1986 PCT Int'l Appl. .

OTHER PUBLICATIONS

G. C. Robin and A. Magora, "Dynamic Analysis of Below-Knee Drop Foot Braces; Studies on Patients with Paralysis of the Lower Limb", Medical & Biological Engineering & Computing, vol. 7, No. 2 (Mar. 1969), pp. 221-226.
S. Miyazaki and H. Iwakura, "Limb-Load Alarm Device for Partial-Weight-Bearing Walking Exercise", Medical & Biological Engineering & Computing, vol. 16, No. 5, (Sep. 1978), pp. 500-505.

Primary Examiner—William E. Kamm
Attorney, Agent, or Firm—Peter K. Kontler

[57] ABSTRACT

A device suitable for monitoring loads exerted on body parts features a measuring device (1) for acquiring a load parameter and an electronic unit (103). The latter possesses an input device (11) for the purpose of entering a load reference range, an analysis device (16), an indicating device (9, 15), a microprocessor (18) and a data memory (19). Fed into the latter are raw data, analysis data derived herefrom, and reference range data. The microprocessor (18), serves to calculate the relationship between momentary-loading and the reference range; the comparative values thus obtained are also stored. From the stored data, and if necessary temporal values, statistical values can be obtained and stored. Indicating device (9,15) permits data to be displayed and stored synchronously. Stored data relating to a load history can be retrieved by means of a retrieval device (11), which permits improved monitoring of loading activities.

29 Claims, 4 Drawing Sheets

DEVICE FOR MONITORING LOADS EXERTED ON PARTS OF THE BODY

The present invention relates to a device suitable for monitoring loading on body members such as the locomotor apparatus of the legs, such device having a measuring apparatus for measuring a load parameter and a portable cordless electronic unit fed with measurement data from the measuring apparatus and comprising an input device for inputting a load reference range. Included also are a computing device and an indicating device, which is used especially for signalling exceeding of the reference range.

The partial removal of loads on the body members plays an important role in treating orthopaedic patients and accident victims. Contusions and compressive injuries to joints, broken bones, injuries to ligaments and tendons, inflammation of the locomotor apparatus as well as wearing down of such parts, or fitting with artificial joints etc. require in part week or month-long partial removal of loading on the affected body part. It is necessary in such cases, to maintain a precise partial load range in order to expedite healing; while excessive loading must be avoided, a minimum load level must be maintained so as to promote the mechanical stimulation required for an optimal healing process. Throughout treatment, the delimited load reference range can be increased.

A device of the above-mentioned type is currently on the market and is described in the brochure "EDAR Insert with Pressure Sensor and Acoustic Feedback" from Harald Haberman Co., Orthopaedic-Technical apparatus, Frankfurt am Main. The conventional battery-driven apparatus possesses a measuring unit in the form of a sole-insert having a pressure sensor. The apparatus emits a low tone when the measured data lie inside the preset reference zone and a high tone whenever this reference zone is surpassed. The patient on crutches can, for example, be acoustically warned by the higher tone should he exert a load upon the locomotor apparatus that is greater than that prescribed by his physician; the deeper tone reassures him that the proper load is being exerted.

The object of the present invention is the further development of the conventional load monitoring device described, with a view to better gauging the loading activity of the patient while permitting continuous long-term load monitoring.

This object is satisfied by the proposed device in that: its data analysis unit features a microprocessor and a data storage area, to which data acquired by the measurement unit, as well as analysis data forming the basis of a load profile, can be fed; analysis data reference values for the establishment of a load reference range can be fed into the storage area from the input device; the momentary load is compared with the reference range and the thus obtained comparative data stored by the electronic unit with the aid of a microprocessor; and the indicating device is designed to function simultaneously with the storage function and/or the stored data relating to a load profile can be retrieved by means of a retrieval device.

The proposed device produces for evaluation not only data relating to the measured load parameters, but also analysis data obtained from such raw data. This has the practical advantage that the loading history can be described more accurately and therefore a more relevant structuring of therapy sessions can be devised. A longer period of overloading, for example, necessitates a different compensatory decrease in the load than a shorter overload interval. On the other hand, the wealth of measurement data permits the acquisition of meaningful analytical data so that the data to be stored and, if necessary, to be compared with the appropriate analysis data reference range, can be reduced in relation to the amount of raw data obtained. This arrangement reduces both the requirement for memory space and the operating time of the microprocessor.

The indicating device allows the patient to monitor his own loading activities and an acoustic signal can be employed to alert the patient should he exceed the load reference zone. This prevents a first feedback means.

The data memory stores the raw data or a portion thereof selected by the microprocessor, together with the analysis data prepared in the microprocessor, as instantaneous or actual load values, so that the relationship of the latter to the appropriate reference zone can be established. The data memory can also store the comparative data obtained. By retrieving all or only selected portions of the stored data, especially the raw and analysis data, as well as the comparative data, the loading activities of the patient throughout a given period can be precisely documented. This arrangement, which permits the patient to monitor his activities during the evening so that he can modify his activities for the next few days, constitutes a second feedback system. If the physician is, upon first meeting the patient, able to review and evaluate his loading behaviour, the patient's chances of recovery are enhanced, therapy sessions can be effectively structured and precise forensic documentation can be undertaken. Depending on the loading behaviour of the patient, the loading reference range can be either raised somewhat or not changed at all during the following period. This arrangement represents a third feedback system. Thus a graduated feedback system is created, which abets optimal therapy structuring.

The measured load parameter is preferably a load force. Suitable load parameters are also an area specific force, i.e. pressure, tensile, shear or bending force. The measured load parameter can also be represented as a kinetic quantity, more particularly the speed or acceleration of a body part, or another physical quantity.

The choice and disposition of the proposed measurement device depends on its use. It is sometimes necessary, for example, to take pressure off the leg or portions thereof. It is advisable if in this case the proposed measurement device be positioned underneath the sole of the foot, whether in the form of an insertable sole, as a therapeutic shoe, or either inside or on the outside of a plaster cast—e.g. in the form of a plaster heel. This type of measuring device can be constructed from two essentially rigid plates, between which are situated three sensors. The presence of the latter affords at once even coverage and the assurance that the entire force will be acquired by the sensors. It is suggested that such plates form an insertable sole, whereby two sensors are arranged near the ball of the foot while the other is arranged in the zone of the heel. The sensors are capable of measuring force or pressure, and can be provided more particularly with strain gauge strips. Such insertable soles could be inexpensively produced as disposable articles suitable for one-time use.

The proposed measuring device can also be fitted to body parts other than the foot, such as the palms of the hands of arthritis patients. The proposed device can also be connected to joints, bones, tendons and ligaments, and is suited for use with artificial joints, bones, tendons, ligaments and parts thereof. It is possible, in these cases, to implant one or more of the proposed devices in the body in order to measure local loading. One or more measuring devices can be positioned between the body and the surface of covers or undercovers, used when the patient sits or lies.

It is furthermore possible to attach one or more measuring devices to an orthotic device or to a mechanical transportation aid, for example to knee braces, underarm crutch supports, axillary crutches or wheelchairs. In such cases, either the load exerted on a given body part, or a load passing by such parts, can be measured.

The apparatus can also be applied to other points, for the purpose e.g. of avoiding long-term overloading damage caused in strenuous sports such as marathons. The device can also be used as a prophylactic against overloading where joints have already been affected (e.g., arthritis), and a worsening of the condition through overloading must be avoided.

It is particularly advantageous if analysis data can be obtained from the measurement data with the aid of the microprocessor. This additional function can be assumed by the microprocessor without great difficulty.

The data used for analysis is largely related to load conditions; included in particular are the maxima of the raw data related to each load cycle. A single load value is derived from the set of raw data processed during the load cycle by the microprocessor.

It is especially advantageous if, in the course of constructing analysis data, the raw data can be correlated with temporal values. This arrangement provides a number of important additional load data.

In particular, the relevant load times of individual load cycles can be used as analysis data. The load time is an important criterion. Should this time period extend beyond a load time reference range, the patient is obliged to alter his loading pattern. An acoustic alarm sounds when this reference range is exceeded. In this connection, the electronic unit, with the aid of the microprocessor, can serve to acquire raw data permitting the monitoring of the time delay occuring between the overstepping and the understepping of a threshold value.

A further analysis parameter can be the impulse magnitudes of the load parameter-time-curve measured in each load cycle. This can be accomplished, in particular, in that the electronic unit, with the aid of the microprocessor, derives a surface integral from the temporally serial raw data. This function can also be assumed with ease by the microprocessor. The magnitude of the impulses represents both the mechanical and temporal load.

It is also advantageous to employ as an analysis datum the number of load cycles occuring within a predetermined period. Where loads are applied to the leg, this parameter is expressed by the number of steps taken. The reference range feature enables the patient to establish an optimal reference range for the number of steps to be taken per day. Aside from the analysis data already mentioned i.e. measurement value maximum, load time, impulse magnetically and cycle count, mathematical functions derived from the latter, be these in conjunction with (or without) time values (such "as per day"), can be employed as analysis data.

A preferred embodiment of the proposed device enables the electronic unit, with the aid of the microprocessor, to produce from the information stored in memory and in conjunction if necessary, with temporal values, statistical data that can appear on the indicator and/or, for the purpose of subsequent retrieval, are fed into memory. Such statistical values compress the load history of the patient and permit either patient or physician to rapidly review and evaluate such information. Such additional work can be handled by the microprocessor without much difficulty.

For these purposes, it is of great help if the analysis data acquired during each load cycle are sorted into classes, of which one is assigned to the reference range, one or more are assigned to an upper range above the reference range and one or more are assigned to a lower range below the reference range. The array of data, thus segregated into classes, is much easier to review.

It is particularly advantageous if a total of five classes be provided, wherein upper range and lower range are each divided into two sub-ranges. Segregation into five classes as opposed to three classes permits not only the determination of the frequency of a patient's either exceeding or falling short of the reference zone, but also the extent to which such exceeding or falling short has occurred.

Thus can be obtained statistical values expressed as percentages, that describe the relationship between the analysis data count obtained in each class and the total number of load cycles over a given period of time. Such percentages clearly indicate the extent to which the patient has or has not adhered to the prescribed reference-range guidelines. This method of interpreting data is particularly suited to indicating raw data maxima, but can also be applied to other analysis data.

Another embodiment permits the maxima of raw data obtained in individual load cycles occuring in a predetermined period to be sorted into load categories and the relevant mean values of the analysis data to be used as statistical values. This arrangement permits certain analysis data such as load times or impulse magnitudes to be compared to maximum raw data values, which opens up further avenues of interpretation.

It is also advantageous if statistical values such as mean analysis data values from all of the load cycles occurring over a predetermined period, are obtained. Such averages aid the doctor considerably in his analysis of data.

It is preferable if both electrical supply and memory have a capacity and a size permitting operation to extend beyond one week. The capacity should permit the essential variables relating to a two week load history to be stored. In order to prevent data loss, the memory should be protected against a power failure.

The indicator advantageously features a viewing window or display, which allows the patient to visually review his load condition and permits more accurate reading of information than afforded by a acoustic signal.

Information retrieved from memory can also be displayed in the window, an arrangement that permits both doctor and patient to review, either at the end of the day or during a visit, prior loading events without exacting special knowledge of computer language or hardware.

Another version of the present invention comprises connecting the electronic part to a printer for the purpose of printing out retreived data. Such printing also does not require any EDP knowledge.

The input and/or retrieval device can also feature a device suitable for storing a programme medium. Such programme media can be reference range or storage retrieval EPROMS.

The input device can also be embodied as a keypad, whereby values can either be entered or retrieved.

In addition, an auxiliary portable measuring amplifier can be connected to the electronic part, in order to process low raw data values, if at the outset of the treatment process a low load reference range has been selected.

It is furthermore advantageous for the microprocessor to possess a means of calibration, by means of which the measuring device can be calibrated. By using the microprocessor, the input device and the display device, it is possible to determine whether or not each sensor has transmitted the correct information and, if not, to correct this error through a correction factor during the evaluation of the raw data.

Concerning the state of the art regarding the related area of indicating the pressure profile of a loaded foot, a measuring system is known that also makes use of sensor-sole inserts in many shoe sizes, but that in addition comprises a large number of sensors for measuring pressure distribution. The evaluation of the information gathered requires considerable hardware and software; the operation of the system requires EDP knowledge and the system itself is conceived for use by orthopaedic surgeons or makers of othopaedic shoes.

The invention is described below with reference to the accompanying drawings which illustrate preferred embodiments of the invention. In the drawings.

Figure 1:
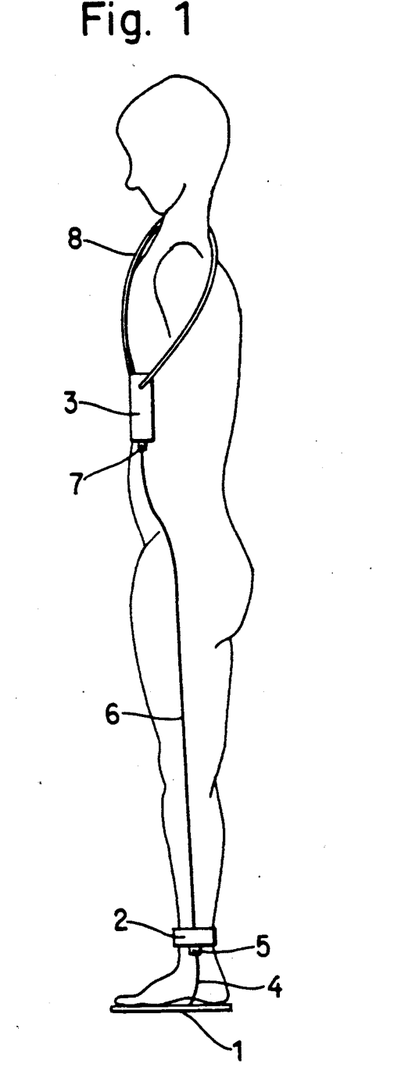
FIG. 1 shows a patient wearing the device according to the invention.
Figure 2:
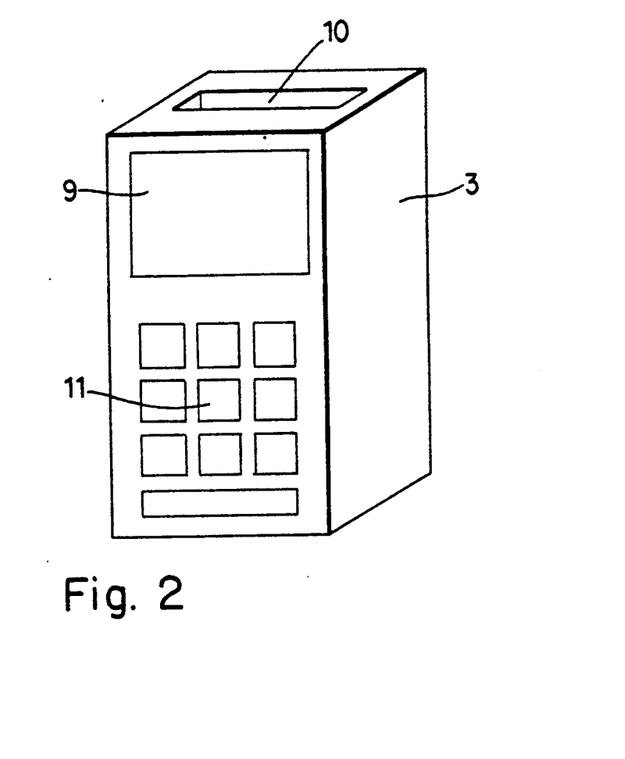
FIG. 2 is a schematic view of the electronic unit.
Figure 3:
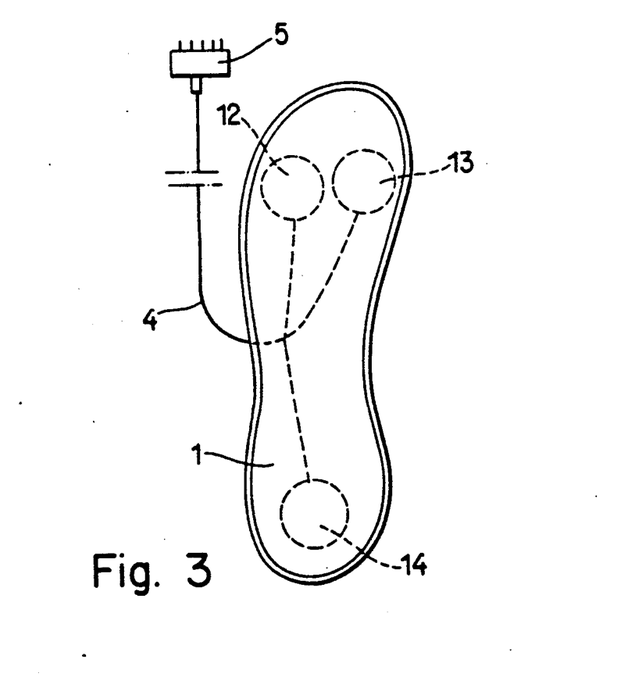
FIG. 3 is a plan view of a measuring device embodied as a disposable insertable sole.

The device shown in FIGS. 1 to 3 comprises a measuring device embodied as an insertable sole 1, a measurement amplifier 2 as well as an electronic unit 3. Leading away from insertable sole 1 is a wire 4 having a connection 5, such wire being sufficiently long to connect measuring device 1 to the measurement amplifier 2 strapped onto the malleolus. A cable 6 having a plug 7 leads from measurement amplifier 2 to electronic unit 3 which advantageously held by means of a carrying loop 8 upon the patient's chest.

The electronic unit 3 shown in FIG. 2 comprises a microprocessor, an indicating system and a data memory which are not shown in detail. The indicating system comprises, in addition to an acoustic indicating device (e.g. a piezo-beeper), an optical indicating device 9 on whose face is a display window. Electronic unit 3 possesses an input device 10, in which can be seen a slot into which a prepared programme medium, such as a reference-range EPROM, can be inserted. Electronic unit 3 is furthermore fitted with a keypad 11, which serves either to input or retrieve data.

Figure 6:
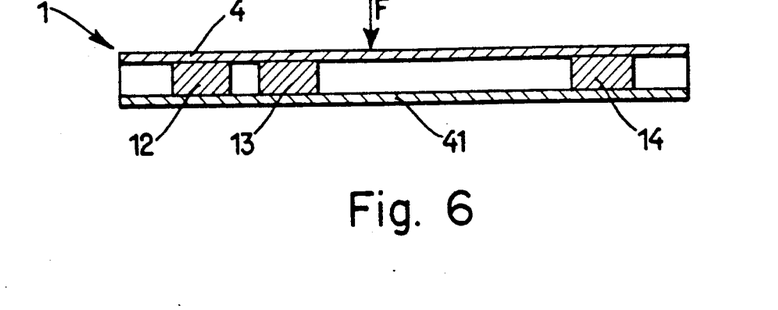
FIG. 6 is a sectional view of the sole of FIG. 3.

The insertable sole of FIGS. 3 and 6 comprises two plates 40, 41 joined together at the edges, located between which are two force sensors 12, 13, in the zone of the ball of the foot, and one force sensor 14 in the zone of the heel, whereby each sensor has a strain measurement strip. The sensors measure the force F acting on the upper plate 40. The sensors are connected to multipole plug 5, which serves not only to transfer raw data through the cable but also to conduct the required current from battery-operated electronic unit 3 or measurement amplifier 2. This modular arrangement, coupled with the simplicity and low cost of the sensors, permits insertable sole 1 to be used as a disposable item.

Figure 4:
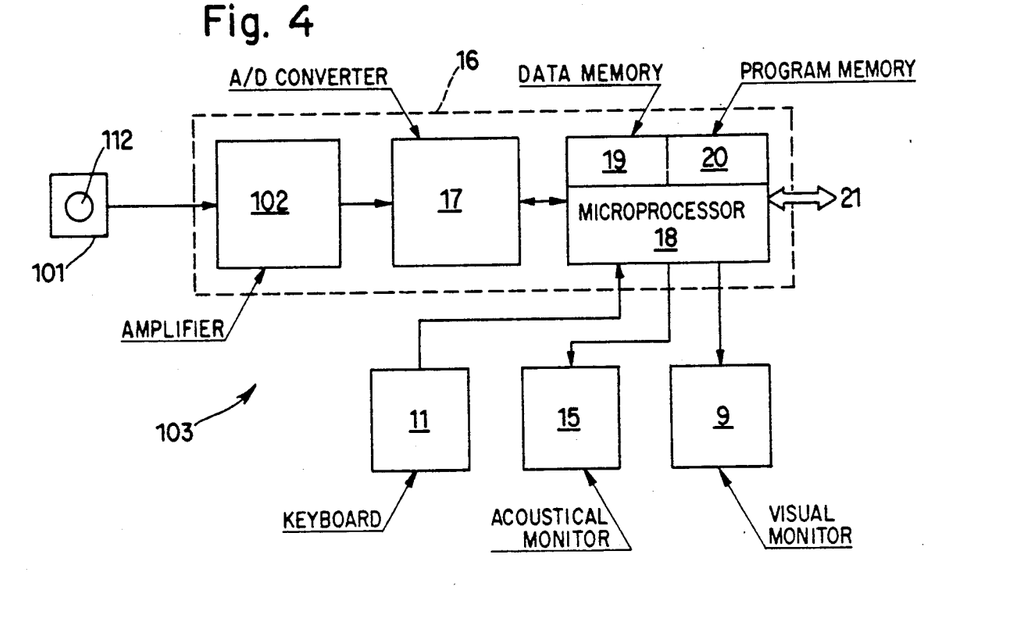
FIG. 4 shows a circuit diagram of the device according to the invention.

The circuit diagram of FIG. 4 corresponds essentially to FIGS. 1 to 3. The measurement amplifier 102, being housed inside electronic unit 103 and not separately, requires the electronic unit to be attached at the ankle or neccessitates the use of a longer cable 4. Measuring device 101 features merely a pressure sensor 112, which is either implanted between two superposed parts of an artificial joint or between two parts of a brace. The other components are identified by the same reference numbers as in the previous figures.

Electronic unit 103 features, in addition to input device 11, which is embodied as a keypad, and to optical indicating device 9, an acoustic indicating device 15 and an evaluating device 16, which comprises measurement amplifier 102, an A/D converter 17, and a microprocessor 18 having a data memory 19 and a programme memory 20. Stored in the latter are the programmes for the microprocessor-controlled processing cycles. Connecting to microprocessor 18 is an I/O interface 21, through which, for example, can be connected a printer for printing out stored data or an external input device for entering commands and data.

Figure 5:
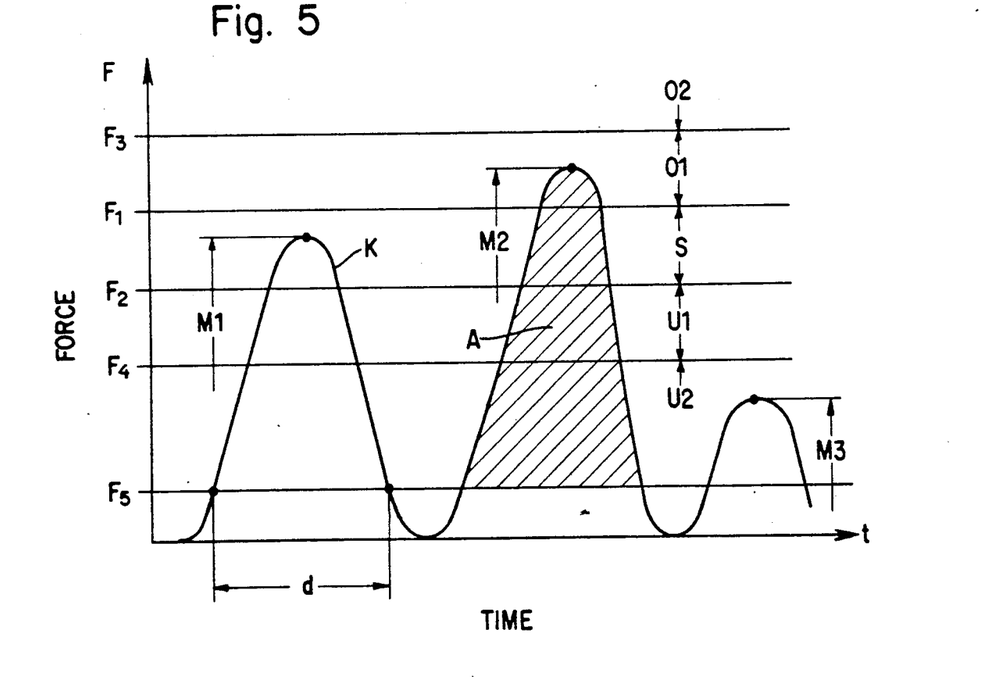
FIG. 5 shows a load time curve.

FIG. 5 shows a load-time curve having a curve constructed from raw data K. Used as an example is load force F acquired by measuring device 1, over a time (t). A load-reference range S is established on the basis of preset boundary values $F_1$, $F_2$ Located above reference range S is an upper range which is divided by boundary value $F_3$ into a near upper range O1 and a further upper range O2. Beneath load reference range S is located a lower range, which is similarly divided by a boundary value $F_4$ into a near lower range U1 and a further lower range U2. A further threshold value $F_5$ is provided in the region of the zero line. The predetermined boundary values can be entered into evaluation device 16 by means of input device 11. The input step is facilitated if a fixed relationship exists e.g. $F_2=0.8\ F_1$; $F_3=1.5\ F_1$; $F_4=0.5\ F_2$ and $F_5=0.1\ F_1$. One need input only $F_1$.

The curve from raw data K obtained from adding the output values of sensors 12, 13, 14 has a continuous path and is tracked over a chronological cycle determined by microprocessor 18; the thus acquired raw data are converted into digital code in the A/D converter 17 and fed into data memory 19. Further analysis data are derived from such raw data with the assistance of microprocessor 18. The raw data fed to the data memory does not have to be permanently stored. The length of time the data is stored depends on the length of time required for analysis or display.

FIG. 5 shows four methods suitable for obtaining analysis data:

a) Each of the raw data maximums is obtained, so that the individual maximums M1, M2, M3 etc. can be used as analysis data.

b) Times are determined, at which the raw values exceed or fall short of threshold value F5. The intervals d thus obtained can be employed as analysis data.

c) The area below curve K is integrated over loading time t. Impulse magnitudes A obtained can also be used as analysis data.

d) The load cycles are counted during a predetermined time period, e.g. during the course of a day. Such cycles are established by observing the number of times threshold value $F_5$ is either exceeded or fallen short of. The load cycle count represents another analysis datum.

The loading history is thus described not only by means of the curve of raw values K, but also by means of the derived analysis data.

The analysis of this loading is described in greater detail in FIG. 5 in connection with example (a). The first maximum M1 lies within reference range S, the second maximum M2 in the near upper zone O1 and the third maximum M3 in the further lower zone U2. In the case of maximum M2, the acoustic indicator device 15 is actuated and an acoustic warning signal is emitted, since the reference range S has been exceeded.

Zones S, O1, O2, U1, U2 constitute load classes. The purpose of subsequent analysis is served if it is determined to which load class each maximum value belongs. It is thus not necessary to know the exact value of the maximum figure. It is sufficient to determine only which of boundary values $F_1$ to $F_5$ was last exceeded. Even this indication can be further simplified through statistical values that demonstrate the number of maxima occurring, during a predetermined time period, in the individual classes, i.e. what percentage of the individual load cycles corresponds to the individual classes. This procedure permits a brief overview of the load history over a predetermined period of time.

It is also possible to evaluate other analysis data by comparison with an analysis-data reference range and the relevant upper and lower zones. It is possible to establish relationships that reveal the mean values of the analysis data within individual load classes.

Concerning the number of load cycles per day, the momentary load value in question is reached only at the end of the period, so that comparison with the reference range begins only at this juncture.

The raw data routed from measuring device 1 as well as the analysis data obtained therefrom, can be caused to appear at any time, and simultaneously with stored data from memory 19, in the optical indication device 9. The relevant comparative data can thus also be displayed, which permits the patient to know at any time if he can increase the load or not, and to what extent this is possible.

After a period of loading, electronic unit 3 is given to the physician, who is able, by means of a retrieval device, e.g. keypad 11, to call up to the indicator device 9, or to a printer, the stored data relating to a particular load history. The physician can use the information acquired on the load history to adjust the load reference range for the following period, and more particularly, to reset the reference ranges for the above-mentioned analysis data in accordance with an optimal treatment regimen.

In one embodiment example, a reference range delimited by an upper and a lower value was input for: the maximum load force; the number of load cycles per day (number of steps) and the total energy expended per day expressed as the sum of all impulse magnitudes, as well as a reference range, delimited only by an upper value, for maximum load duration (step duration). A warning signal is produced whenever the reference ranges for load force and step duration are exceeded.

The patient is thus able at anytime, by pressing a button on keypad 11, to view on the optical display 9 the momentary load force, the load reference ranges (especially for load force and number of steps), the average value of the maximum current day load and the current day's step count. The patient can review in the morning the overloading occurring on the previous day, represented by the number of excesses and the maximum value (expressed as a percentage deviation from the reference value), as well as the number of steps taken on the previous day, expressed by the step count and a deviation in percent.

The physician can, in a brief interrogation session, review from the already entered reference ranges, the daily counts since the last visit, the average number of steps taken per day, the average size of the load force maximums as well as the three highest individual loads. It is furthermore possible to recall the maximum and minimum number of load cycles occurring per day and the maximum and minimum average load forces per day. Moreover, a special interrogation session can serve to identify what percentage of the load cycles reached their maximum values M1, M2, M3 within the individual load categories, the size of the average duration d of all load cycles as well as the durations of the load cycles in each of the load categories, and the average value of the total energy (expressed as the sum of the impulse magnitudes) expended per day as well as the percentage of total energy apportioned to each class. Such information affords the physician a good overview of the load history.

In conclusion, analysis data, obtained from the raw data, not only corresponds to the extent, duration, impulse magnitude and number of individual loads, but can be mathematical functions derived from one, two or three such values, and can be expressed as functions of such values measured and/or derived over a period of time (e.g. "per day"), whereby such values can be routed to data memory 19 as well, as indicating device 9. For certain kinds of load, expressible as raw or analysis data, reference value ranges can be input through input device 10 or 11. The actual value of such loads (momentary loads) are compared, with the aid of the microprocessor, with the input reference ranges. Comparative data are also fed to data memory 19 and can be routed in real time to indicator devices 9, 15. Statistical values are obtained from stored actual values, comparative data and other temporal values (e.g. number of days), with the aid of microprocessor 18. Such statistical values can be routed in real time to both the indicating devices 9, 15 and data memory 19. A certain combination of reference range, actual values, temporal values and statistical values causes one or more types of acoustical signal to be produced by acoustic signal device 15, while certain information is displayed in the optical display device.

The size of the battery or accumulator and that of the data memory 19 permit electronic apparatus 103 to function for one, two or more weeks, which allows storage of the entire load history occurring between two serial visits to the doctor. The type of memory system used, or an auxiliary battery, ensure the protection of memorized data and the continuous running of the clock.

The calibration of the measuring device entails a calibration routine being entered with the aid of keypad 11. In this mode, each force sensor 12, 13, 14 is loaded with a standard force. This calibration, can be accomplished, for example, by subjecting the sensor to loading by a local-area pressure body, whereby a weighing scale positioned underneath indicates a predetermined reference value. If the latter does not appear in the indicating device 9, the display must be altered by keypad manipulation until the desired reference value appears. The result of this arrangement is that all other data from the sensor in question can be corrected for error by an adjustment member employed by the microprocessor.

Shown in the embodiment examples is that measuring device 1 is connected to electronic unit 3 by means of cable 4, 6. Alternatively, a transmitter can be integrated in the measuring device and a receiver in the electronic unit for the purpose of remote data transfer.

Commercially-available components are used in the circuitry. The following components, for example, have been used:

Force sensor 12, 13, 14: Type 125 SF sensor with strain gauge strip—SK-06-125GF-20C from Measurement Group.
A/D Transformer 17: MAX 134 from Maxim
Microcomputer with microprocessor 18, data memory 19 and programme memory 20:DS 5000 from Dallas Semiconductors.

Figure 7:
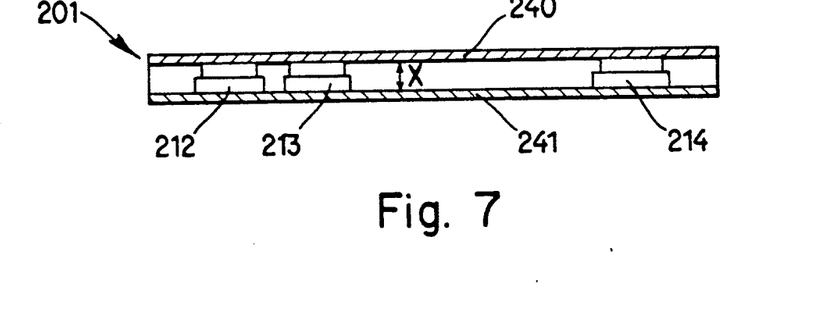
FIG. 7 is similar to FIG. 6 but shows another embodiment of the sole.

FIG. 7 shows an insertable sole 201 which comprises a pair of spaced plates 240,241. Three displacement sensors 212,213,214 are sandwiched between the plates 240,241 and measure the distance x between the latter.

Figure 8:
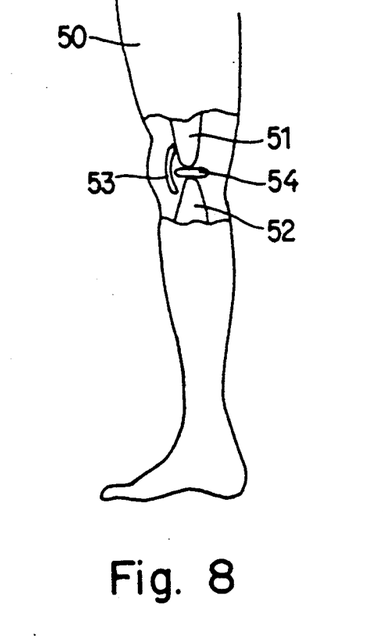
FIG. 8 shows a measuring device which is embodied as an implant for a knee joint.

FIG. 8 illustrates a measuring device 54 serving as an implant in the knee joint of a leg 50. The measuring device 54 is disposed between the femur 51 and the tibia 52 behind the knee cap 53.

Figure 9:
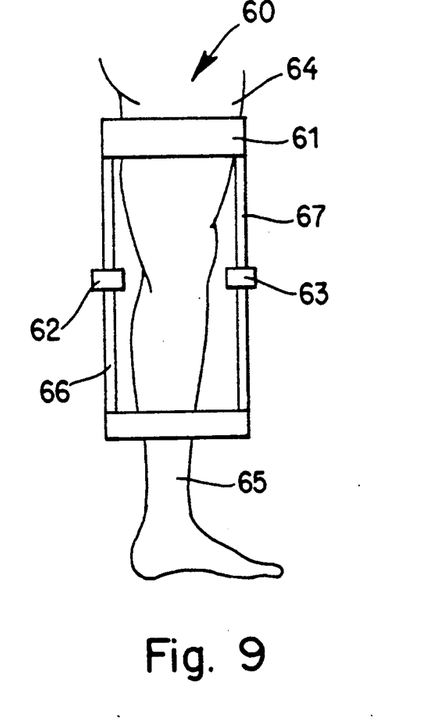
FIG. 9 shows a pair of measuring devices which are embodied as components of a knee brace.

FIG. 9 shows a knee brace 61 which is secured to the thigh 64 and shank 65 of a leg 60. The knee is bridged by connecting rods 66,67 and measuring devices 62,63 are incorporated in the respective rods 66,67.

Figure 10:
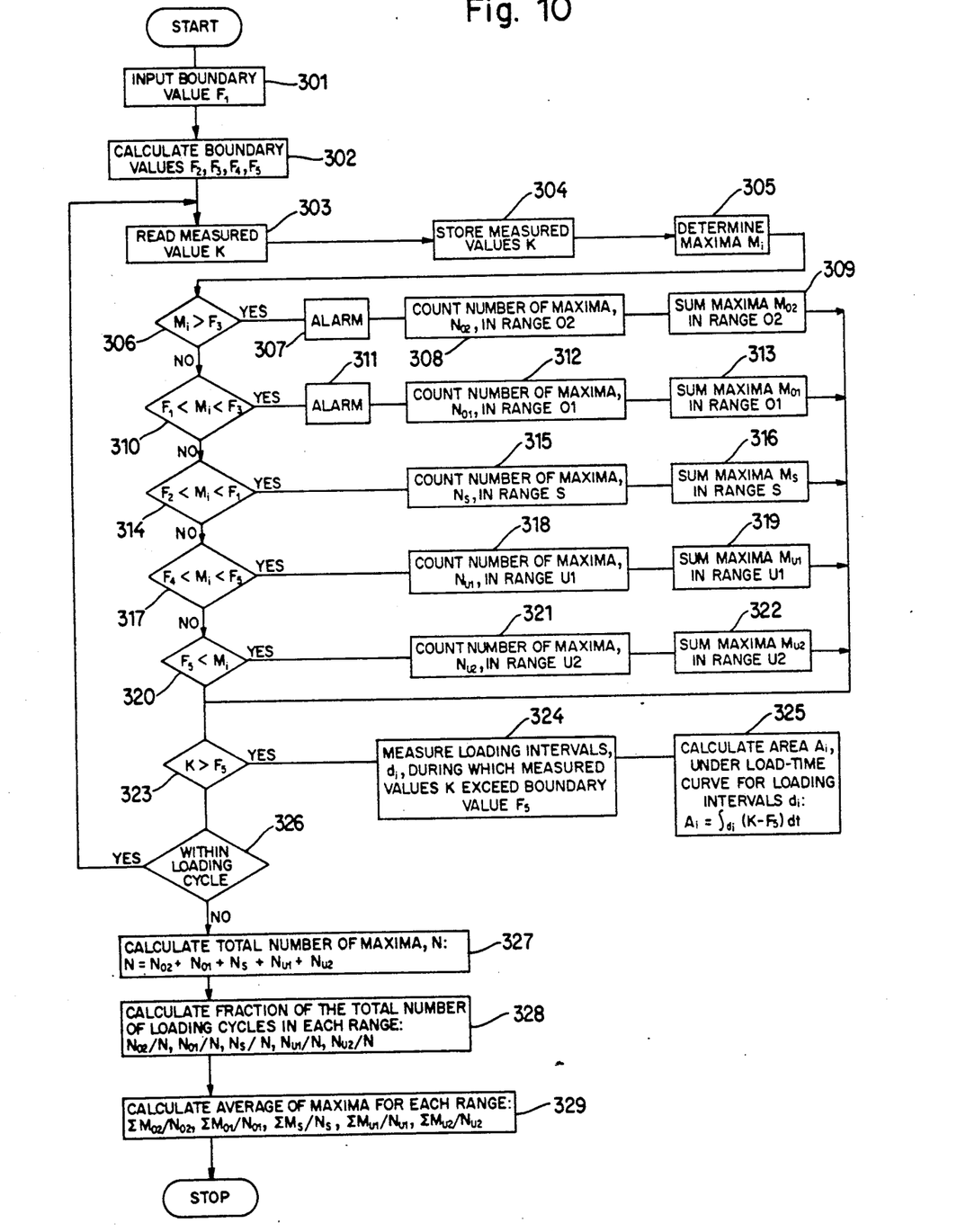
FIG. 10 is an algorithm illustrating the operation of the monitoring device in accordance with the invention.

The operation of the monitoring device according to the invention is described below with reference to the exemplary algorithm of FIG. 10 and the exemplary load-time diagram of FIG. 5.

The algorithm starts with the input of the boundary value $F_1$ in step 301. Next, the boundary values $F_2, F_3, F_4, F_5$ are calculated per step 302.

The measuring values K are read in step 303 and stored in step 304. The maxima $M_i$ are determined in step 305.

The maxima are evaluated in steps 306 to 322 to establish the ranges O2,O1,S,U1,U2 in which the respective maxima are located. When a maximum exceeds the boundary value $F_i$ an alarm goes off as in steps 307 and 311. In steps 308,312,315,318 and 321, the number of maxima in the respective ranges O2,O1,S,U1,U2 are counted. To permit calculation of average values for the maxima, the individual maxima in each range O2,O1,S,U1,U2 are summed.

In steps 323 to 325, the intervals, $d_i$, during which the measured values K exceed the boundary value $F_5$ are determined and the area under the load-time curve for these loading intervals is obtained by integration.

A determination as to whether the loading cycle was exceeded is made in step 326. The algorithm returns to step 303 if the answer is in the affirmative while analysis proceeds if the answer is no.

In the first part of the analysis at step 327, the total number of maxima is calculated. The fraction of the total number of loading cycles in each range O2,O1,S,U1,U2 can then be obtained as in step 328. In step 329, the average of the maxima is calculated for each range. This completes the algorithm.

I claim:

1. A device for monitoring loads on parts of the body, comprising a first unit for measuring a load-related parameter and generating raw data representing the parameter; and a portable, off-line, electronic second unit having a microprocessor, a memory for analysis data representing loading history, means for entry of the raw data in said memory, and means for entering reference data in said memory and producing a visual representation of data in said memory, said microprocessor having means for comparing instantaneous load-related data with a reference range derived from the reference data, and means for transferring the resulting comparative data to said memory.

2. The device of claim 1, wherein said first unit comprises a force sensor.

3. The device of claim 1, wherein said first unit comprises a pressure sensor.

4. The device of claim 1, wherein said first unit comprises a displacement sensor.

5. The device of claim 1, wherein said first unit at least in part constitutes a foot support.

6. The device of claim 5, wherein said first unit comprises a pair of essentially rigid plates, and three sensors between said plates.

7. The device of claim 6, wherein said first unit at least in part constitutes an insole, two of said sensors being disposed in the region of the ball of the foot and the other of said sensors being disposed in the region of the heel.

8. The device of claim 1, wherein said first unit at least in part constitutes an implant.

9. The device of claim 1, wherein said first unit at least in part constitutes a mechanical aid for the body.

10. The device of claim 1, wherein said microprocessor comprises means for generating at least a portion of the analysis data, said generating means including means for processing the raw data so as to produce such portion of the analysis data.

11. The device of claim 1, wherein said second unit comprises means for generating at least a portion of the analysis data, said generating means including means for establishing the maxima of the raw data during respective loading cycles.

12. The device of claim 1, wherein said second unit comprises means for generating at least a portion of the analysis data, said generating means including means for evaluating the variation of the raw data with time.

13. The device of claim 12, wherein said evaluating means comprises means for establishing the periods of loading during respective loading cycles.

14. The device of claim 13, wherein said microprocessor comprises means for establishing the interval between a time at which the raw data rises above a threshold value and a time at which the raw data falls below the threshold value.

15. The device of claim 12, wherein said evaluating means comprises means for establishing impulse magnitudes during respective loading cycles from a plot of the load-related parameter versus time.

16. The device of claim 15, wherein said microprocessor comprises means for integrating at least a portion of the raw data over time.

17. The device of claim 12, wherein said evaluating means comprises means for establishing the number of loading cycles within a predetermined interval of time.

18. The device of claim 1, wherein said microprocessor comprises means for statistically analyzing at least a portion of the data in said memory and said entering and producing means comprises means for generating a visual representation of the resulting statistical values.

19. The device of claim 18, wherein said second unit comprises means for assigning analysis data for a loading cycle to different ranges selected from the reference range, an upper range above the reference range and a lower range below the reference range.

20. The device of claim 19, wherein said analyzing means comprises means for calculating the amount of analysis data in each range as a percentage of the total number of loading cycles within a predetermined time interval.

21. The device of claim 18, wherein the analysis data includes the raw data maxima of individual loading cycles and said second unit comprises means for assigning the analysis data of the loading cycles within a predetermined time interval to different load ranges, said analyzing means comprising means for averaging the analysis data in each range.

22. The device of claim 18, wherein said analyzing means comprises means for averaging the analysis data of all loading cycles within a predetermined time interval.

23. The device of claim 1, further comprising a power source; and wherein said power source and said memory have respective capacities sufficient for at least one week of operation.

24. The device of claim 1, wherein said entering and producing means comprises a viewing screen.

25. The device of claim 24, wherein said entering and producing means comprises means for retrieving data from said memory and reproducing the retrieved data on said screen.

26. The device of claim 1, wherein said entering and producing means comprises means for connecting said second unit to a printer so as to print out a loading history.

27. The device of claim 1, wherein said entering and producing means comprises means for accommodating a program carrier.

28. The device of claim 1, wherein said entering and producing means comprises a keyboard.

29. The device of claim 1, wherein said second unit is provided with a calibration routine for said first unit and said microprocessor comprises means for calibrating said first unit with said calibration routine.

* * * * *